United States Patent
Botzer et al.

(10) Patent No.: US 11,311,226 B2
(45) Date of Patent: Apr. 26, 2022

(54) DETECTION OF VENTRICULAR ACTIVITY USING UNIPOLAR AND BIPOLAR SIGNALS

(71) Applicant: BIOSENSE WEBSTER (ISRAEL) LTD., Yokneam (IL)

(72) Inventors: Lior Botzer, Timrat (IL); Vladimir Rubinstein, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 151 days.

(21) Appl. No.: 16/712,415

(22) Filed: Dec. 12, 2019

(65) Prior Publication Data
US 2021/0177293 A1 Jun. 17, 2021

(51) Int. Cl.
*A61B 5/287* (2021.01)
*A61B 5/316* (2021.01)
*A61B 5/00* (2006.01)

(52) U.S. Cl.
CPC .............. *A61B 5/287* (2021.01); *A61B 5/316* (2021.01); *A61B 5/6869* (2013.01)

(58) Field of Classification Search
CPC ........... A61B 5/287; A61B 5/24; A61B 5/316; A61B 5/318; A61B 5/339; A61B 5/346; A61B 5/367; A61B 5/6869; A61B 5/6852; A61B 5/743; A61B 5/352
See application file for complete search history.

(56) References Cited

U.S. PATENT DOCUMENTS

| | | | |
|---|---|---|---|
| 2013/0281870 A1 | 10/2013 | El Haddad | |
| 2015/0208938 A1 | 7/2015 | Houben | |
| 2015/0208942 A1 | 7/2015 | Bar-Tal | |
| 2016/0183824 A1* | 6/2016 | Severino | A61B 5/7246 600/523 |
| 2018/0042505 A1 | 2/2018 | Botzer | |
| 2021/0145346 A1* | 5/2021 | Holmes, III | A61B 5/7257 |

FOREIGN PATENT DOCUMENTS

EP 2901923 A1 8/2015

OTHER PUBLICATIONS

European Search Report for corresponding EPA No. 20213462.3 dated Mar. 18, 2021.
Kelley P. Anderson et al., "Determination of Local Myocardial Electrical Activation for Activation Sequence Mapping. A Statistical Approach", Circulation Research, vol. 69, No. 4, Oct. 1, 1991, pp. 898-917.

* cited by examiner

*Primary Examiner* — Scott M. Getzow

(57) ABSTRACT

A method includes receiving a bipolar signal sensed by a pair of electrodes at a location in a heart of a patient. A unipolar signal is received, which is sensed by an electrode at the location in the heart. A derivative of the received bipolar signal is computed. A derivative of the received unipolar signal is computed. A ratio is evaluated, between the derivative of the bipolar signal and the derivative of the unipolar signal at local minima of the derivative of the unipolar signal. When the ratio is smaller than a preset threshold ratio value, an occurrence of ventricular activity is indicated.

16 Claims, 2 Drawing Sheets

DETECTION OF VENTRICULAR ACTIVITY USING UNIPOLAR AND BIPOLAR SIGNALS

FIELD OF THE INVENTION

The present invention relates generally to electrophysiological signals, and specifically to a method for evaluation of electrical propagation in the heart.

BACKGROUND OF THE INVENTION

Recording of unipolar and bipolar electrical signals from the heart was previously suggested in the patent literature. For example, U.S. Patent Application Publication 2018/0042505 describes a method, including receiving a bipolar signal from a pair of electrodes in proximity to a myocardium of a human subject, and receiving a unipolar signal from one of the pair of electrodes. The method further includes delineating a window of interest (WOI) for the unipolar and bipolar signals, within the WOI computing local unipolar minimum derivatives of the unipolar signal, and times of occurrence of the local unipolar minimum derivatives, and within the WOI computing bipolar derivatives of the bipolar signal at the times of occurrence. The method also includes evaluating ratios of the bipolar derivatives to the local unipolar minimum derivatives, and when the ratios are greater than a preset threshold ratio value, assigning the times of occurrence as times of activation of the myocardium, counting a number of the times of activation and classifying the unipolar signal according to the number.

As another example, U.S. Patent Application Publication 2015/0208938 describes a bipolar electrogram and a unipolar electrogram that are recorded from electrodes of a probe, and differentiated with respect to time. Peaks are identified in the differentiated bipolar electrogram. An activity window is defined that includes bipolar activity about the peaks. An extreme negative value in the differentiated unipolar electrogram within the activity window is reported as a unipolar activation onset. In one aspect, an annotation is selected from candidate minima in the differentiated unipolar electrogram within the activity window by excluding candidates that fail to correlate with activity in the bipolar electrogram.

U.S. Patent Application Publication 2015/0208942 describes diagnostic catheterization of the heart that includes recording a bipolar electrogram and a unipolar electrogram from an electrode on the catheter at a location in the heart, and defining a window of interest wherein a rate of change in a potential of the bipolar electrogram exceeds a predetermined value. An annotation is established in the unipolar electrogram, wherein the annotation denotes a maximum rate of change in a potential of the unipolar electrogram within the window of interest. A quality value is assigned to the annotation, and a 3-dimensional map is generated of a portion of the heart that includes the annotation and the quality value thereof.

U.S. Patent Application Publication 2013/0281870 describes a method for characterizing an electrocardiogram, including receiving a first unipolar signal from a first location of a heart and a second unipolar signal from a second location of the heart. A bipolar signal is generated from the first and second unipolar signals, and analyzed to delineate a time period during which the first and second locations generate a bipolar complex. The method also includes analyzing the first unipolar signal within the time period to determine an activation time of the first location.

SUMMARY OF THE INVENTION

An exemplary embodiment of the present invention that is described herein provides a method including receiving a bipolar signal sensed by a pair of electrodes at a location in a heart of a patient. A unipolar signal is received, which is sensed by an electrode at the location in the heart. A derivative of the received bipolar signal is computed. A derivative of the received unipolar signal is computed. A ratio is evaluated, between the derivative of the bipolar signal and the derivative of the unipolar signal at local minima of the derivative of the unipolar signal. When the ratio is smaller than a preset threshold ratio value, an occurrence of ventricular activity is indicated.

In some exemplary embodiments, receiving the bipolar signal includes receiving multiple bipolar signals from multiple electrode pairs of a multielectrode catheter, and further includes comparing time differences between the multiple bipolar signals, and, when the time differences are smaller than a prespecified value, indicating an occurrence of ventricular activity.

In some exemplary embodiments, receiving the unipolar signal includes receiving multiple unipolar signals from multiple electrodes of a multielectrode catheter, and the method further includes, if time differences between the unipolar signals are smaller than a prespecified value, indicating an occurrence of ventricular activity.

In an exemplary embodiment, receiving the unipolar signal includes receiving the unipolar signal from one of the electrodes in the pair.

In another exemplary embodiment, computing the ratio includes defining a time interval including a window-of-interest and computing the ratio within the window-of-interest.

In some exemplary embodiments, the method further includes alerting a user of the indication of the occurrence of ventricular activity.

In some exemplary embodiments, the method further includes presenting the bipolar signals to a user, with an annotation thereon indicative of the ventricular activity.

In other exemplary embodiments, the method further includes analyzing successive bipolar signals in time, and indicating the occurrence of ventricular activity only when the ratio is maintained smaller than a preset threshold ratio value for at least a prespecified duration.

There is additionally provided, in accordance with an exemplary embodiment of the present invention, an apparatus including an interface and a processor. The interface is configured to receive a bipolar signal from a pair of electrodes placed at a location in a heart of a patient, and receive a unipolar signal from an electrode placed at the location in the heart. The processor is configured to (a) compute a derivative of the received bipolar signal, (b) compute a derivative of the received unipolar signal, (c) evaluate a ratio between the derivative of the bipolar signal and the derivative of the unipolar signal at local minima of the derivative of the unipolar signal, and (d) when the ratio is smaller than a preset threshold ratio value, indicate an occurrence of ventricular activity.

The present disclosure will be more fully understood from the following detailed description of the embodiments thereof, taken together with the drawings, in which:

BRIEF DESCRIPTION OF THE DRAWINGS

The present invention will be more fully understood from the following detailed description of the embodiments thereof, taken together with the drawings, in which.

DETAILED DESCRIPTION OF EMBODIMENTS

Overview

Figure 1:
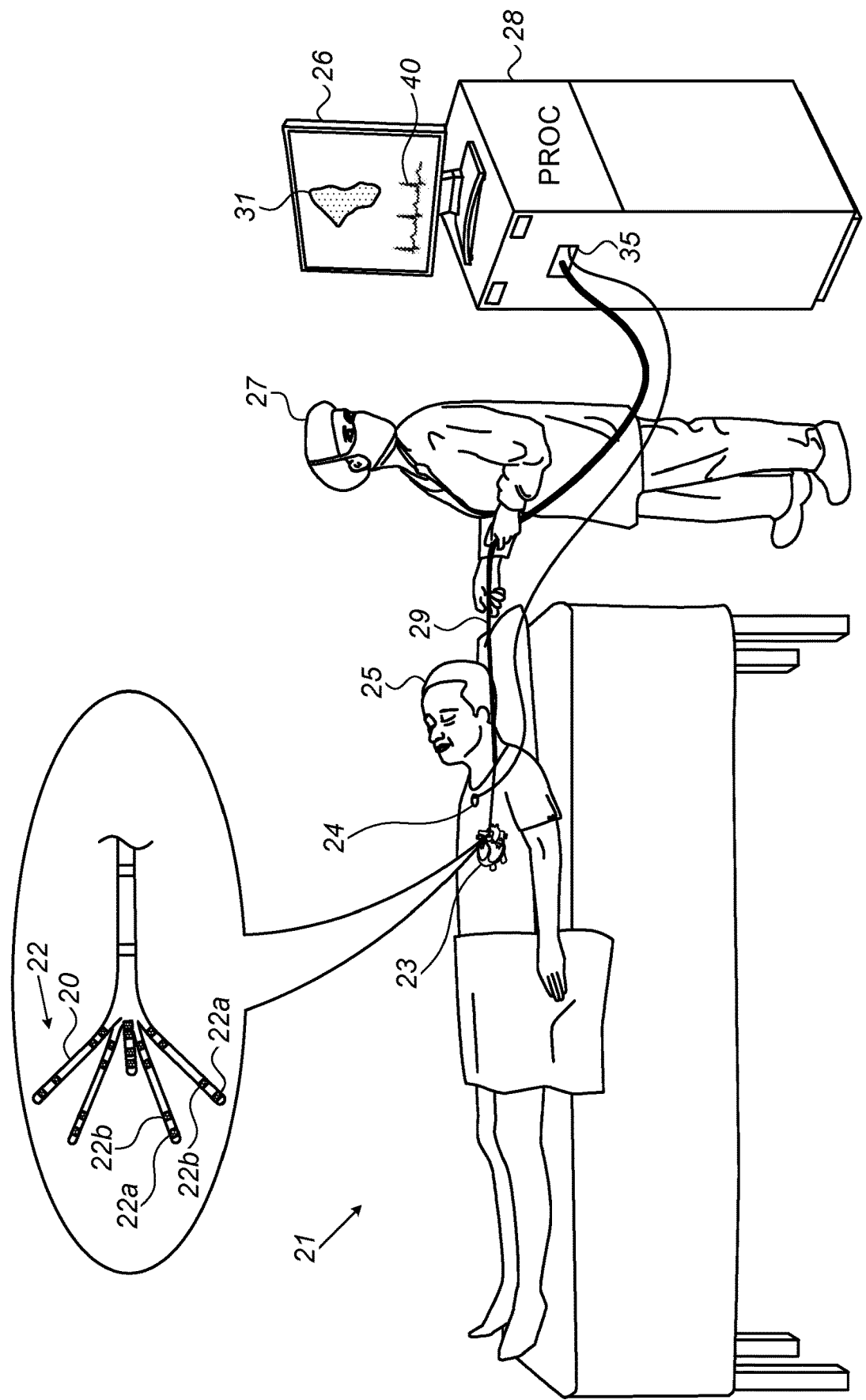
FIG. 1 is a schematic, pictorial illustration of a catheter-based electrophysiological (EP) mapping system, in accordance with an exemplary embodiment of the present invention.

An electrophysiological (EP) signal acquired from the heart using a catheter may typically be a combination of near-field and far-field bio-electric signals. Clinically, however, the near-field signal is usually more significant. Moreover, some far-field signals are considered interference that may corrupt near-field sensed signals. For example, when acquiring signals from a catheter positioned in an atrium of the heart, a physician needs to know when ventricular far-field activity is intruding on near-field signals.

In the present context, a near-field bio-electric signal is a signal received from cardiac tissue at a local point of contact of a diagnostic electrode with tissue. A far-field bio-electric signal is a signal from a region distant from the contacted tissue region. Typically, such a far-field bio-electric signal propagates by conduction through blood and is sensed by the diagnostic electrode of the catheter while the electrode acquires the near-field signal via contact with tissue.

Exemplary embodiments of the present invention that are described hereinafter provide a method and apparatus for the detection of transient far-field ventricular activity. In some exemplary embodiments, a processor receives bipolar signals sensed by a pair of electrodes of the catheter placed in contact with diagnosed tissue, such as of the left atrium of the heart, and a unipolar signal sensed by an electrode of the same catheter, or another catheter placed in contact with the cardiac tissue.

Ventricular activity is typically shown by a sharp change in the unipolar signal while a milder change occurs in the bipolar signal. Therefore, if the slope of the unipolar signal is strong, but at the same time the slope of the bipolar signal is small, this behavior is suspected to result from transient far field ventricle activity.

In some exemplary embodiments, the processor first computes the derivatives of the received bipolar and unipolar signals, and then computes a ratio between the derivative of the bipolar signal and the derivative of the unipolar signal. By comparing the calculated ratio to a preset threshold, the processor identifies an occurrence of interfering far-field ventricular activity, e.g., when the ratio is lower than a preset threshold ratio value. The processor then indicates the occurrence of ventricular activity to a user. In an exemplary embodiment, the ratio is a dynamic ratio that the processor can update based on, for example, a level of noise in an acquired signal.

In some exemplary embodiments, the electrode that senses the unipolar signal is one of the aforementioned electrode pair. In other exemplary embodiments, the unipolar signal is received using one or more ECG surface leads.

In some exemplary embodiments, the processor defines a time interval comprising a window-of-interest, and computes a ratio of the received unipolar signal to the bipolar signal within that window-of-interest. Alternatively or additionally, the processor computes a ratio of the slopes of received unipolar signal to that of the bipolar signal within that window-of-interest.

In some cases, local bio-electric signals can show similarities with far field bio-electric signals. In some exemplary embodiments, to distinguish local activity from far field activity, the processor analyzes bio-electric signals from multiple electrode pairs of a multielectrode catheter (such as a PentaRay™ catheter, made by Biosense Webster). If the signals result from far field activity, the timing of signals should be similar across the different electrode pairs, while if the signals result from local activity, signals would be dispersed in time, e.g., separated of each other in time by more than a prespecified value.

In some exemplary embodiments the processor is further configured to alert or mark for the physician that a ventricle activity was detected. The system can further use this in order to select or exclude beats from acquisition.

The disclosed method for the detection of ventricular activity relies on a proposition that ventricular activity may typically occur if there a large unipolar signal sensed or a large change in the unipolar signal sensed, while at the same time there is a small bipolar signal, or there is a small change in bipolar signal, respectively, or more quantitatively, if the ratio of either of the two pairs of signals is above a given threshold.

In an exemplary embodiment, the processor analyzes successive bipolar signals in time and if the ratio between the derivative of the bipolar signals and the derivative of at least one of the respective unipolar signals is maintained smaller than a preset threshold ratio value for at least a prespecified duration, the processor indicates an occurrence of ventricular activity and only if so.

Typically, the processor is programmed in software containing a particular algorithm that enables the processor to conduct each of the processor related steps and functions outlined above.

The disclosed method for the detection of ventricular activity may improve the value of diagnostic catheterization procedures by enabling a physician to discard corrupted bio-electric sensed signals.

System Description

FIG. 1 is a schematic, pictorial illustration of a catheter-based electrophysiological (EP) mapping system 21, in accordance with an exemplary embodiment of the present invention. FIG. 1 depicts a physician 27 using an electro-anatomical mapping catheter 29 to perform an electro-anatomical mapping of a heart 23 of a patient 25. Mapping catheter 29 comprises, at its distal end, one or more arms 20, each of which is coupled to a bipolar electrode 22 comprising adjacent electrodes 22a and 22b.

During the mapping procedure, the locations of electrodes 22 are tracked while they are inside the heart 23 of the patient. For that purpose, electrical signals are passed between electrodes 22 and external electrodes 24. For example, three external electrodes 24 may be coupled to the patient's chest, and another three external electrodes may be coupled to the patient's back. (For ease of illustration, only one external electrode is shown in FIG. 1.)

Based on the signals, and given the known positions of electrodes 24 on the patient's body, processor 28 calculates an estimated location of each electrode 22 within the patient's heart 23. Respective electrophysiological data, such as intracardiac ECG traces, are additionally acquired from tissue of the heart 23 by using electrodes 22. The processor may thus associate any given signal received from electrodes 22, such as an electrophysiological signal, with the location at which the signal was acquired. The processor 28 receives the resulting signals via an electrical interface 35, and uses information contained in these signals to construct an electrophysiological map 31 and ECG traces 40, and to present these on a display 26.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 28 runs a dedicated algorithm as disclosed herein, including the process illustrated in FIG. 3, that enables processor 28 to perform the disclosed steps, as further described below.

The example illustration shown in FIG. 1 is chosen purely for the sake of conceptual clarity. Other types of electrophysiological sensing catheter geometries, such as the Lasso® Catheter (produced by Biosense-Webster Inc., Irvine, Calif.) may be employed. Additionally, contact sensors may be fitted at the distal end of mapping catheter 29 and transmit data indicative of the physical quality of electrode contact with tissue. In an exemplary embodiment, measurements of one or more electrodes 22 may be discarded if their physical contact quality is indicated as poor, and the measurements of other electrodes may be regarded as valid if their contact quality is indicated as sufficient.

Detection of Ventricular Activity Using Unipolar and Bipolar Signals

Figure 2:
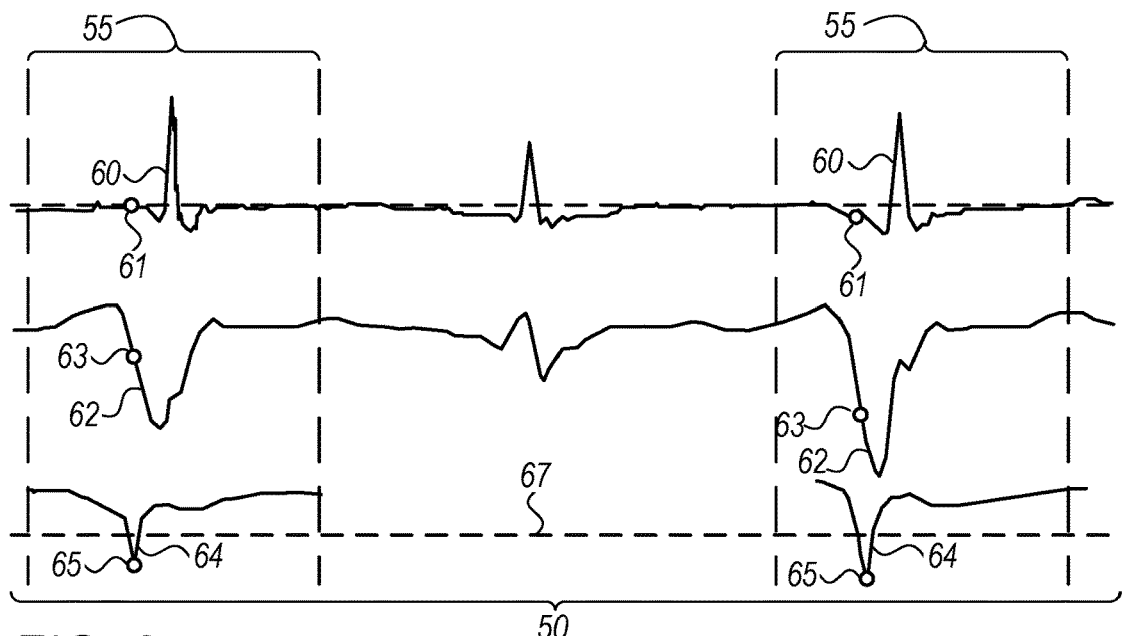
FIG. 2 is a graph of bipolar and unipolar electrocardiogram (ECG) signals recorded using the system of FIG. 1, and of a calculated respective ratio of unipolar to bipolar ECG signals, according to an exemplary embodiment of the present invention.

FIG. 2 is a graph of bipolar (60) and unipolar (62) electrocardiogram (ECG) signals recorded using system 21 of FIG. 1, and of a calculated respective ratio (64) of unipolar to bipolar ECG signals, according to an exemplary embodiment of the present invention. Bipolar signal 60 is received from a pair of electrodes 22 of catheter 29, and unipolar signal 62 received from a selected electrode from the electrode pair. The shown signals are received over a time interval 50 with two windows-of-interest (WOI) 55 shown within interval 50, all defined by processor 28. Processor 28 calculates ratio 64 of the bipolar derivative signal to the bipolar derivative signal within WOI 55 and compares calculated ratio 64 to a preset threshold (or dynamic threshold) 67, so as to identify far-field ventricular activity. In the illustrated exemplary embodiment, processor 28 indicates the occurrence of far-field ventricular activity (i.e., when ratio 64 falls lower than threshold 67), by annotations 61, 63, and 65 overlaid on the ratio graph (64). However, additional graphical means and actions taken by processor 28 (such as tagging the signals within the WOI for future processing), are possible.

Figure 3:
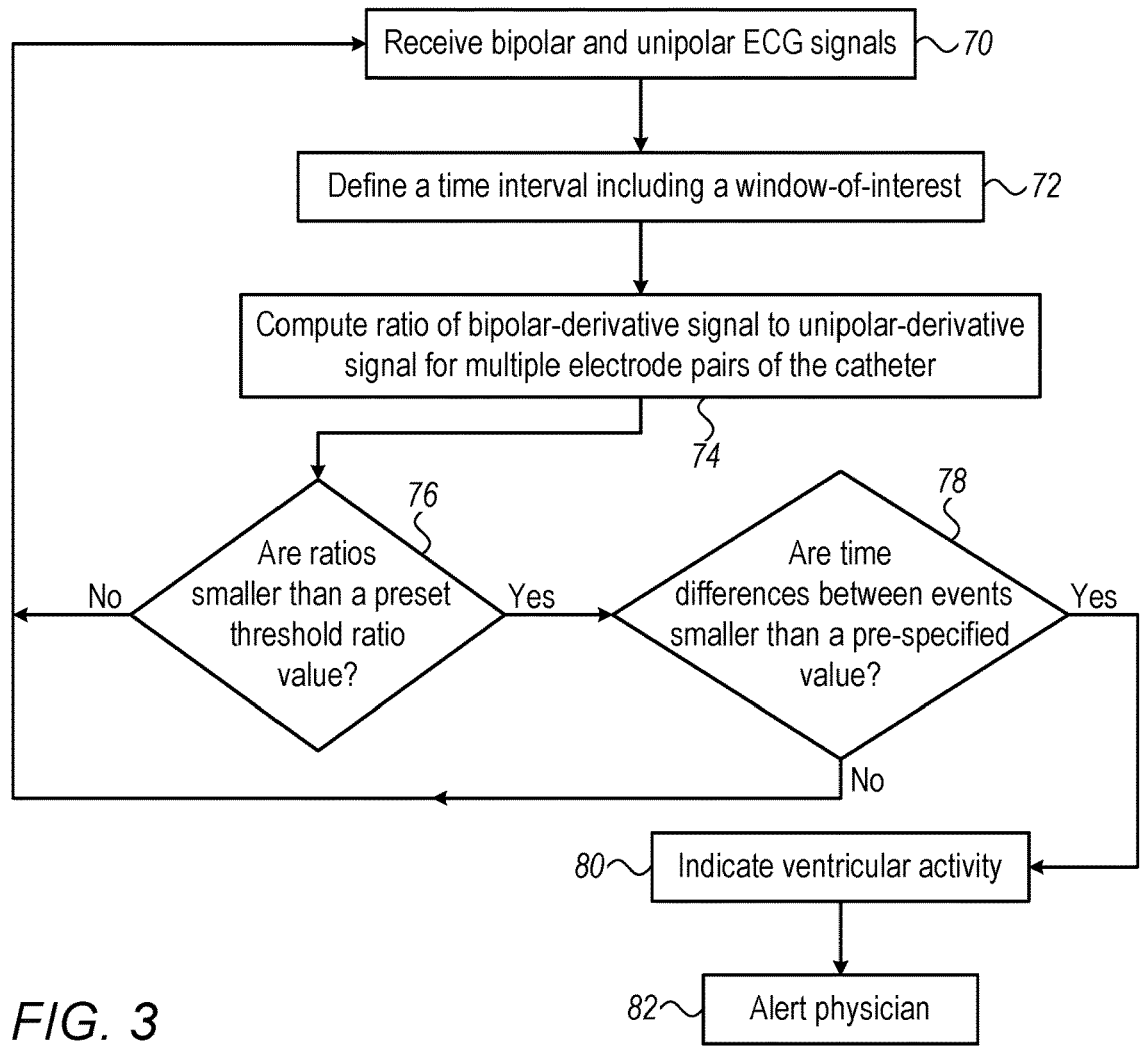
FIG. 3 is a flow chart that schematically illustrates a method and algorithm for the detection of far-field ventricular activity, according to an exemplary embodiment of the present invention.

FIG. 3 is a flow chart that schematically illustrates a method and algorithm for the detection of far-field ventricular activity, according to an exemplary embodiment of the present invention. The algorithm, according to the presented exemplary embodiment, carries out a process that begins with processor 28 receiving bipolar and unipolar ECG signals from catheter 29, at a data receiving step 70. Next, processor 28 defines a time interval 50 that includes WOI 55, at a data selection step 72. Then, processor 28 calculates a ratio 64 of the bipolar-derivative to the unipolar-derivative signals, at a ratio calculation step 74 for multiple electrode pairs. At a checking step 76, processor 28 checks for each electrode pair if ratio 64 falls below preset threshold value 67. If the answer is no for at least a given fraction of electrode pairs of those considered, the process returns to step 70 to new signals. If the answer is yes for sufficient fraction of the electrode pairs the process continues.

To distinguish local bio-electric activity from far field bio-electric activity, the processor compares the timing of the valid fraction of bio-electric signals. If at a checking step 78, the analysis shows that the timing of signals is dissimilar across the different electrode pairs, and the processor concludes that the signals result from local activity and the process returns to step 70 to collect new signals.

If time differences between the signals are smaller than a prespecified value, processor 28 concludes that the signals result from transient far-field activity, and indicates the detected ventricular activity, for example, by performing annotations 61, 63, and 65, at a ventricular activity indicating step 80. Finally, using various possible audiovisual means, processor 28 alerts physician 82 of the detected ventricular activity. In some embodiments, the processor compares different unipolar signals received and if the time differences between different unipolar signals are found by the processor to be smaller than a prespecified duration, the processor indicates an occurrence of ventricular activity.

The example flow chart shown in FIG. 3 is chosen purely for the sake of conceptual clarity. The present embodiment may also comprise additional steps of the algorithm, such as receiving multiple bipolar and unipolar ECG signals, as well as receiving indication of the degree of physical contact of the electrodes with diagnosed tissue from a contact force sensor. This and other possible steps are omitted from the disclosure herein purposely on order to provide a more simplified flow chart.

Although the exemplary embodiments described herein mainly address cardiac diagnostic applications, the methods and systems described herein can also be used in other medical applications, such as in defibrillators and pacers.

It will be appreciated that the exemplary embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for detection of ventricular activity using unipolar and bipolar signals, the method comprising:
receiving a bipolar signal sensed by a pair of electrodes at a location in a heart of a patient;
receiving a unipolar signal sensed by an electrode at the location in the heart;
computing a derivative of the received bipolar signal;
computing a derivative of the received unipolar signal;
evaluating a ratio between the derivative of the bipolar signal and the derivative of the unipolar signal at a local minima of the derivative of the unipolar signal, wherein the derivative of the bipolar signal is the numerator of the ratio and the derivative of the unipolar signal is the denominator of the ratio; and when the ratio is smaller than a preset threshold ratio value, indicating an occurrence of ventricular activity.

2. The method according to claim 1, wherein receiving the bipolar signal comprises receiving multiple bipolar signals from multiple electrode pairs of a multielectrode catheter, and comprising comparing time differences between the multiple bipolar signals, and, when the time differences are smaller than a prespecified value, indicating an occurrence of ventricular activity.

3. The method according to claim 1, wherein receiving the unipolar signal comprises receiving multiple unipolar signals from multiple electrodes of a multielectrode catheter, and comprising, if time differences between the unipolar signals are smaller than a prespecified value, indicating an occurrence of ventricular activity.

4. The method according to claim 1, wherein receiving the unipolar signal comprises receiving the unipolar signal from one of the electrodes in the pair.

5. The method according to claim 1, wherein computing the ratio comprises defining a time interval comprising a window-of-interest and computing the ratio within the window-of-interest.

6. The method according to claim 1, and comprising alerting a user of the indication of the occurrence of ventricular activity.

7. The method according to claim 1, and comprising presenting the bipolar signals to a user, with an annotation thereon indicative of the ventricular activity.

8. The method according to claim 1, and comprising analyzing successive bipolar signals in time, and indicating the occurrence of ventricular activity only when the ratio is maintained smaller than a preset threshold ratio value for at least a prespecified duration.

9. An apparatus for detection of ventricular activity using unipolar and bipolar signals, the apparatus comprising:

an interface, which is configured to receive a bipolar signal from a pair of electrodes placed at a location in a heart of a patient, and receive a unipolar signal from an electrode placed at the location in the heart; and a processor configured to:

compute a derivative of the received bipolar signal;

compute a derivative of the received unipolar signal;

evaluate a ratio between the derivative of the bipolar signal and the derivative of the unipolar signal at a local minima of the derivative of the unipolar signal, wherein the derivative of the bipolar signal is the numerator of the ratio and the derivative of the unipolar signal is the denominator of the ratio; and when the ratio is smaller than a preset threshold ratio value, indicate an occurrence of ventricular activity.

10. The apparatus according to claim 9, wherein the processor is configured to receive the bipolar signal by receiving multiple bipolar signals from multiple electrode pairs of a multielectrode catheter, compare time differences between the multiple bipolar signals, and, when the time differences are smaller than a prespecified value, indicate an occurrence of ventricular activity.

11. The apparatus according to claim 10, wherein the processor is configured to receive the unipolar signal by receiving multiple unipolar signals from multiple electrodes of a multielectrode catheter, and, if time differences between the unipolar signals are smaller than a prespecified value, indicate an occurrence of ventricular activity.

12. The apparatus according to claim 9, wherein the processor is configured to receive the unipolar signal from one of the electrodes in the pair.

13. The apparatus according to claim 9, wherein the processor is configured to define a time interval comprising a window-of-interest and compute the ratio of the unipolar signal to the bipolar signal within the window-of-interest.

14. The apparatus according to claim 9, wherein the processor is further configured to alert a user of the indication of the occurrence of ventricular activity.

15. The apparatus according to claim 9, wherein the processor is further configured to present the bipolar signal to a user, with an annotation thereon indicative of the ventricular activity.

16. The apparatus according to claim 9, wherein the processor is further configured to analyze successive bipolar signals in time, and indicate the occurrence of ventricular activity only when the ratio is maintained smaller than a preset threshold ratio value for at least a prespecified duration.

* * * * *